United States Patent
Conti

(10) Patent No.: US 12,257,363 B2
(45) Date of Patent: Mar. 25, 2025

(54) MEDICAL DEVICE FOR NEURAL REPAIRING OF THE SPINAL CORD OR OF A NERVE

(71) Applicant: Michele Conti, Nogaredo (IT)

(72) Inventor: Michele Conti, Nogaredo (IT)

(73) Assignee: Michele Conti, Nogaredo (IT)

( * ) Notice: Subject to any disclaimer, the term of this patent is extended or adjusted under 35 U.S.C. 154(b) by 1032 days.

(21) Appl. No.: 17/269,237

(22) PCT Filed: Aug. 30, 2019

(86) PCT No.: PCT/IB2019/057332
§ 371 (c)(1),
(2) Date: Feb. 17, 2021

(87) PCT Pub. No.: WO2020/044304
PCT Pub. Date: Mar. 5, 2020

(65) Prior Publication Data
US 2021/0322640 A1  Oct. 21, 2021

(30) Foreign Application Priority Data
Aug. 30, 2018 (IT) .................. 102018000008253

(51) Int. Cl.
*A61L 27/36* (2006.01)
*A61L 27/18* (2006.01)
(Continued)

(52) U.S. Cl.
CPC .......... *A61L 27/3675* (2013.01); *A61L 27/18* (2013.01); *A61L 27/225* (2013.01); *A61L 27/303* (2013.01);
(Continued)

(58) Field of Classification Search
CPC .... A61L 27/3675; A61L 27/18; A61L 27/225; A61L 27/303; A61L 27/306; A61L 27/3834; A61L 27/54; A61L 27/3878
See application file for complete search history.

(56) References Cited

U.S. PATENT DOCUMENTS 5,609,629 A * 3/1997 Fearnot ................. A61L 27/306
 623/1.42
9,238,090 B1 * 1/2016 Fette ....................... A61L 27/56
(Continued)

FOREIGN PATENT DOCUMENTS

KR 20140024025 A 2/2014

OTHER PUBLICATIONS

European Patent Office, International Search Report issued in PCT/IB2019/057332, mailed Dec. 16, 2019, Rijswijk, NL.
(Continued)

*Primary Examiner* — Erin McGrath
(74) *Attorney, Agent, or Firm* — Ferguson Case Orr Paterson

(57) ABSTRACT

A medical device for repairing injuries to the spinal cord or peripheral nerve has a first flexible substrate supporting first nanoparticles selected from the group consisting of silicon, carbon, gold and titanium, at least partially embedded in a binding layer joined to the first flexible substrate. Each first nanoparticle develops along a preferential direction of development. The nanoparticles are oriented so that, statistically, the preferential direction of development is parallel to a first orientation of growth. Stem cells are at least partially embedded in the binding layer. The first nanoparticles are functionalized so that stem cell differentiation along the first nanoparticles is guided in the first orientation of growth. The first flexible substrate is suitable to assume a distended configuration and a wrapped configuration in which it is wrapped around the spinal cord or peripheral
(Continued)

nerve whereby the first orientation of growth is statistically parallel to the neuronal direction of extension of neurons of the spinal cord or peripheral nerve.

3 Claims, 4 Drawing Sheets

(51) Int. Cl.
*A61L 27/22* (2006.01)
*A61L 27/30* (2006.01)
*A61L 27/38* (2006.01)
*A61L 27/54* (2006.01)

(52) U.S. Cl.
CPC ......... *A61L 27/306* (2013.01); *A61L 27/3612* (2013.01); *A61L 27/362* (2013.01); *A61L 27/3625* (2013.01); *A61L 27/3834* (2013.01); *A61L 27/3878* (2013.01); *A61L 27/54* (2013.01); *A61L 2300/414* (2013.01); *A61L 2400/12* (2013.01); *A61L 2420/04* (2013.01); *A61L 2430/32* (2013.01)

(56) References Cited

U.S. PATENT DOCUMENTS

| | | | |
|---|---|---|---|
| 2002/0155096 A1* | 10/2002 | Chancellor | A61L 27/3834 |
| | | | 435/366 |
| 2006/0204738 A1* | 9/2006 | Dubrow | A61F 13/02 |
| | | | 428/292.1 |
| 2009/0148417 A1 | 6/2009 | Kim et al. | |
| 2010/0068240 A1 | 3/2010 | Chiu et al. | |
| 2010/0144004 A1* | 6/2010 | Zhong | C12M 25/10 |
| | | | 435/395 |
| 2012/0045512 A1 | 2/2012 | Lee et al. | |
| 2012/0149112 A1 | 6/2012 | Feng et al. | |
| 2013/0204393 A1* | 8/2013 | Samaniego | A61L 27/3687 |
| | | | 623/23.72 |

OTHER PUBLICATIONS

Novikova et al., Biodegradable poly-β-hydroxybutyrate scaffold seeded with Schwann cells to promote spinal cord repair, Biomaterials, Mar. 2008, pp. 1198-1206, vol. 29, Issue 9, Elsevier Science Publishers B.V., Barking, GB.

Gerburg Keilhoff et al., Neuronal NOS deficiency promotes apoptotic cell death of spinal cord neurons after peripheral nerve transection, Nitric Oxide, Mar. 2004, pp. 101-111, vol. 10, Issue 2, Elsevier.

European Patent Office, Written Opinion issued in PCT/IB2019/057332, mailed Dec. 16, 2019, Rijswijk, NL.

Italian Search Report issued in 201800008253, mailed May 16, 2019.

* cited by examiner

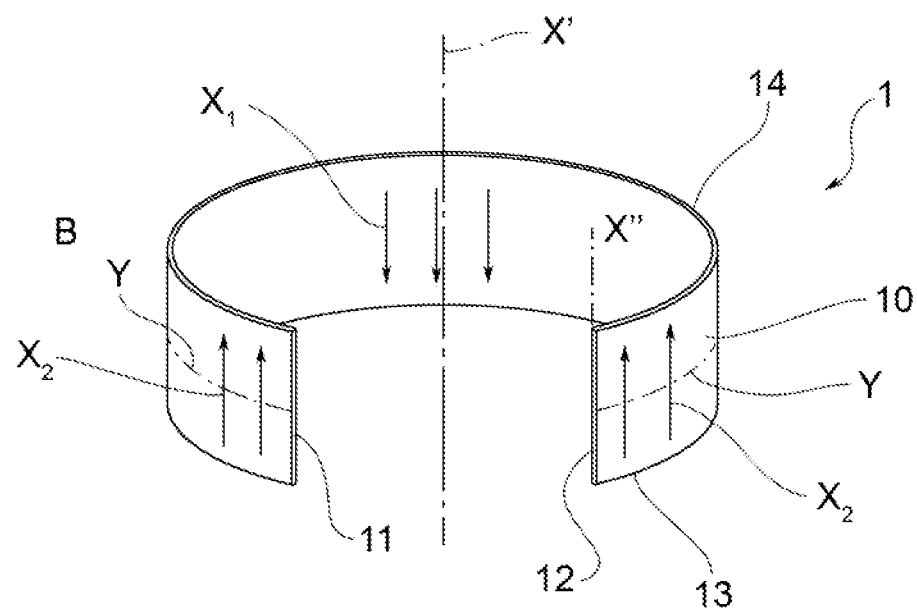
FIG.2
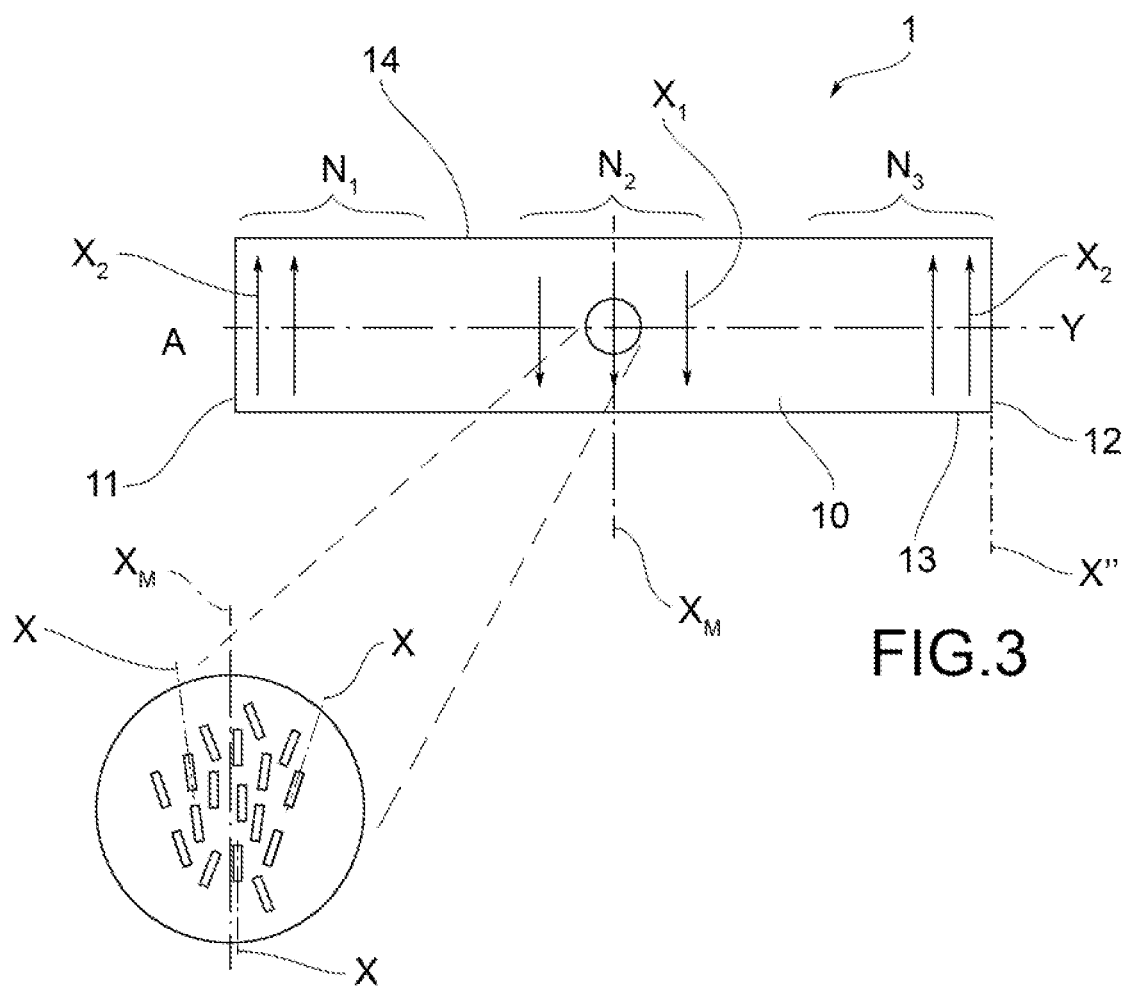
FIG.3
FIG.3a

MEDICAL DEVICE FOR NEURAL REPAIRING OF THE SPINAL CORD OR OF A NERVE

CROSS-REFERENCE TO RELATED APPLICATIONS

This application is a National Phase Application of PCT International Application No. PCT/IB2019/057332, having an International Filing Date of Aug. 30, 2019 which claims the benefit of priority to Italian Patent Application No. 102018000008253, filed Aug. 30, 2018, each of which is hereby incorporated by reference in its entirety.

FIELD OF THE INVENTION

The present invention relates to a medical device for the neural repair of the spinal cord or a damaged or diseased peripheral or cranial nerve.

BACKGROUND OF THE INVENTION

Neuropathologies are known to degenerate and damage the nervous system, particularly the neurons in the brain, in the spinal cord and in the peripheral nervous system. Damage to or alteration of the neural network leads to the creation of anomalous structures and functionality with a drastic reduction in the quality of life. With regard to damage to the neural network of the spinal column (known as spinal cord injury) there is a strong need to explore new therapeutic strategies to treat this pathology. Damage to the spinal cord is linked to two types of lesions: 1) primary lesions involving physical damage immediately following a traumatic event, such as lacerations, contusions, compressions and contractions of neuronal tissue; 2) secondary lesions resulting from primary lesions that may affect long-term mobility; this type of lesion is characterized by inflammatory processes, alterations in local ionic concentration, loss of the local vascular system resulting in decreased blood flow and penetration of serum proteins into the spinal cord. These changes lead to demyelisation, ischemia, necrosis and apoptosis of the neuronal tissue of the spinal cord.

The current strategies developed have led to therapies that act on primary, secondary or both lesions; the main objective is to block the cascade mechanisms in place during secondary lesions. In particular, a wide variety of therapies have been developed to alter the neuro-inflammatory process, reduce free radical damage, improve blood flow and counteract the effects of local ionic changes. All therapies targeting secondary lesions are based on the use of active drugs or molecules (e.g. myelin, associated with glycoproteins or inhibitors).

Within this scenario, with the numerous clinical studies carried out, only the therapy with glucocorticoid methylprednisolone (MP) seems to be effective, albeit in a limited way and with limited improvements in the patients treated.

Due to new therapeutic methodologies and the discovery of new nanotechnological applications, part of the research is currently focused on a regenerative as well as therapeutic approach, in particular aimed at the regeneration of axons. In particular, attempts have been made to promote neuronal regrowth by directly applying autologous stem cells in the vicinity of the neuronal lesion, however without obtaining effective results.

Although the use of nanoparticles to promote growth and differentiation of stem cells in vitro, such as those described in US2009148417A1 or KR20140024025A, is known in the art, it is not known how to promote the growth and differentiation of stem cells directly on lesions of the peripheral or central nerves or the spinal cord.

SUMMARY OF THE INVENTION

The need for a device and a method capable of improving and promoting neuronal regeneration through the use of stem cells directly on a lesion of a spinal cord or a peripheral or central nerve is therefore strongly felt.

The aforesaid objects are achieved by a medical device as described and claimed herein.

Preferred embodiments are also described.

In another aspect, the aforesaid objects are also achieved by a surgical method for the implantation of the medical device according to the present invention.

BRIEF DESCRIPTION OF THE DRAWINGS

The features and advantages of the medical device and the surgical method will be apparent from the description given below, provided by way of non-limiting example, in accordance with the accompanying figures, wherein:

FIG. 2 shows schematically a perspective view of a medical device in accordance with an embodiment of the present invention, in a partially wrapped configuration;

FIG. 3 shows schematically a planar view of the medical device of FIG. 2 in a distended configuration;

FIG. 3a schematically shows an exaggerated enlargement of a region of the medical device in FIG. 3, whereby the arrangement of nanoparticles is schematically visible;

DETAILED DESCRIPTION

Figure 1:
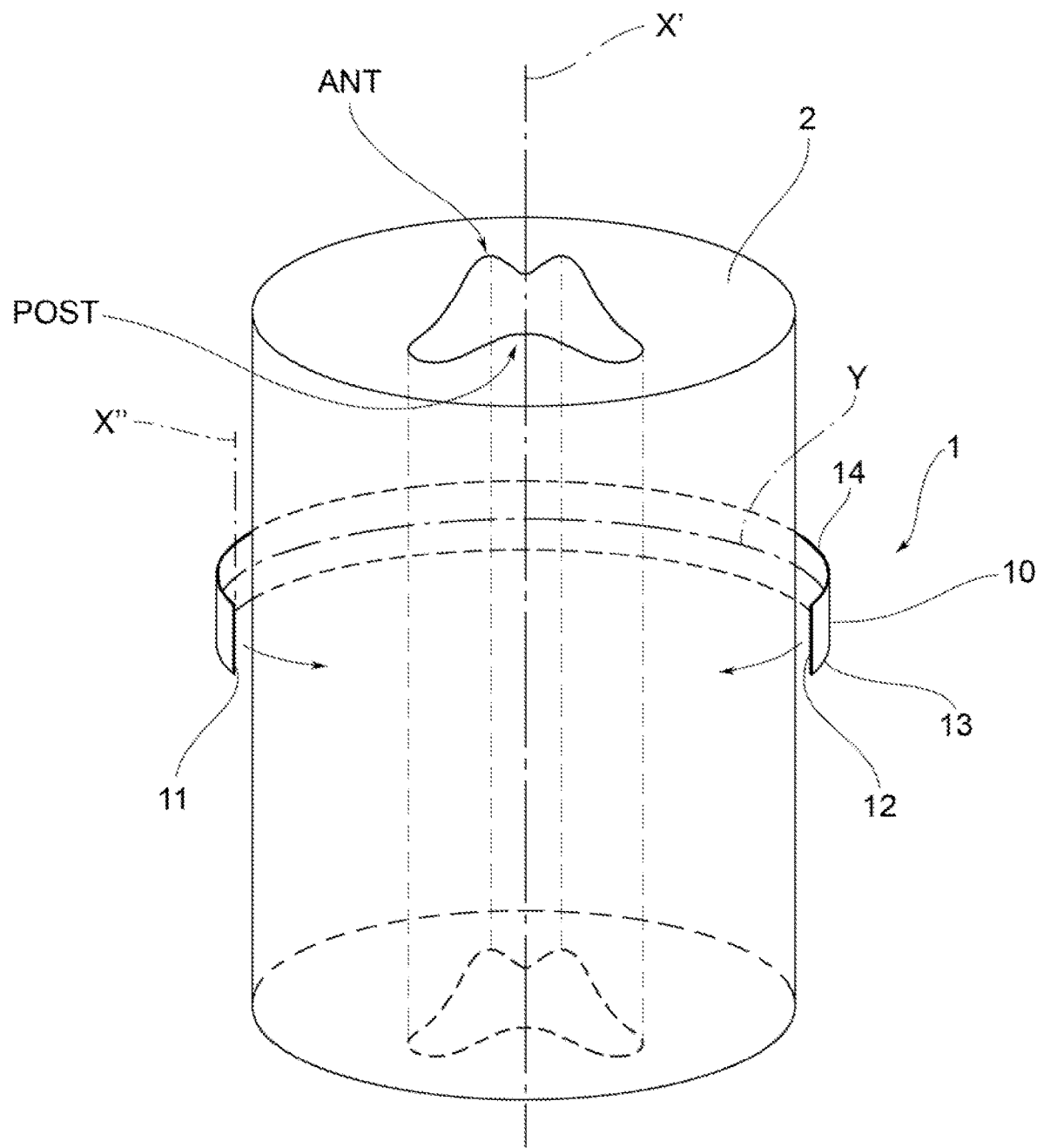
FIG. 1 shows schematically a perspective view of a medical device in accordance with an embodiment of the present invention, in a step of implantation around the spinal cord.

In accordance with the accompanying figures, a medical device for the repair of a lesion in the spinal cord 2 or in a peripheral nerve is indicated collectively at 1.

The medical device comprises a first flexible biocompatible or biological substrate 10 that supports first nanoparticles of silicon, or carbon or gold or titanium. The first flexible substrate is, for example, a thin (less than a millimeter), flexible strip made of biological or biocompatible material.

The first nanoparticles are at least partially or totally embedded in a binding layer 20, made of binding material, joined to the first flexible substrate 10. The binding material comprises, for example, fibrin and may therefore be a fibrin or Lyodura or polyamide or polylactide glue or an equivalent material, for example enriched with growth factors. Stem cells are at least partially embedded in the binding layer 20, preferably autologous stem cells from the patient on whom the medical device is to be implanted.

Each nanoparticle develops along a preferential direction of development X. Moreover, the nanoparticles are oriented in such a way that, statistically, the preferential direction of development X of each nanoparticle is substantially parallel to a first orientation of growth X1 of the stem cells.

The first nanoparticles are functionalized in such a way that the differentiation of such stem cells along said first nanoparticles is guided in the first orientation of growth X1.

The term "functionalized" or "functionalize" in the present document means the process, known to the person skilled in the art, of adding new functions, characteristics, capabilities or properties to a material by changing the chemistry or morphology of the material. It is a technique used in chemistry, materials science, biological engineering, textile engineering and nanotechnology. Functionalization may be performed, for example, by creating a particular form of the nanoparticle, or by attaching or adsorbing molecules on the nanoparticle or by treating the surface of the nanoparticle (e.g. with specific "coatings"), sometimes with a chemical bond but sometimes only through adsorption or surface treatment. All this is done in the aim of guiding the differentiation and proliferation of the stem cells.

The first flexible substrate 10 is suitable to assume a distended configuration A and a wrapped configuration B. In particular, before being implanted, the first flexible substrate 10 is preferably in the distended configuration A, while, once implanted, the device is arranged in a configuration wrapped around the spinal cord or peripheral nerve. It is clear that a distended configuration should therefore be understood as a generic configuration of the flexible substrate in the pre-implantation stage, different from the configuration wrapped around the spinal cord. In the case wherein the flexible substrate is a thin strip, the distended configuration A is a planar configuration, while in the wrapped configuration B, the thin strip assumes an annular shape around the spinal cord or nerve, as shown for example in FIG. 1.

In the wrapped configuration B, the first flexible substrate 10 is wrapped around the spinal cord 2 or a peripheral nerve whereby the first orientation of growth X1 is substantially statistically parallel to the neuronal direction X' of extension of the neurons of the spinal cord or peripheral nerve.

In the present document, the term "statistically" means that in a statistical way there is a predominance of orientation of the nanoparticles in one orientation or in one direction (for example in the first orientation of growth X1), or that the first orientation of growth X1 is substantially parallel to a statistically predominant direction of extension of the neurons in the spinal cord. For example, the statistical comparison to determine the parallelism could be evaluated by calculating an average 3D axis of extension of the neuron bundle of the nerve or of the spinal cord or an average axis of orientation of the nanoparticles XM, calculated as the average or median 2D or 3D axis of all preferential directions of development X of the nanoparticles, as, for example, shown in FIG. 3a).

Preferably, the device comprises second nanoparticles of silicon, or carbon or titanium or gold, at least partially embedded in the binding layer 20. Such nanoparticles are arranged in such a way that, statistically, the preferential direction of development X of each second nanoparticle is substantially parallel to a second orientation of growth X2, and wherein said second nanoparticles are functionalized to guide the differentiation of the stem cells in the orientation opposite to the orientation of differentiation in the first orientation of growth X1.

In an advantageous embodiment of the present invention, the first orientation of growth X1 is the efferent (or craniocaudal) orientation of the neurons and the second orientation of growth X2 is the afferent (or caudo-cranial) orientation of the neurons.

Preferably, therefore, in the case of a first thin, flexible substrate 10, on this flexible substrate are arranged in succession and adjacent to each other functionalized regions containing nanoparticles statistically oriented alternately in the first orientation of growth X1 and in the second orientation of growth X2.

For example, as shown in FIG. 3, the medical device 1 comprises a first region N1, near to a left end 11 of the first flexible substrate 10, wherein the second nanoparticles are oriented in such a way that the preferential direction of development X of each nanoparticle is statistically parallel to the second orientation of growth X2 of the stem cells. Moreover, in this region N1, the second nanoparticles are functionalized in such a way that the differentiation of such stem cells along said second nanoparticles is guided in the second orientation of growth X2. Moreover, the medical device 1 comprises a second region N2, adjacent to the first region N1 and arranged more toward the center of the first flexible substrate 10, wherein the first nanoparticles are oriented in such a way that the preferential direction of development X of each nanoparticle is statistically parallel to the first orientation of growth X1 of the stem cells. Moreover, in this region N2, the first nanoparticles are functionalized in such a way that the differentiation of such stem cells along said first nanoparticles is guided in the first orientation of growth X1 opposite to the second orientation of growth X2.

Preferably, moreover, the medical device 1 comprises a third region N3, near to a right end 12 of the first flexible substrate 10, wherein third nanoparticles are oriented in such a way that the preferential direction of development X of each third nanoparticle is statistically parallel to a third orientation of growth of the stem cells, preferably identical to the second orientation of growth X2. Moreover, in this region N3, the third nanoparticles are functionalized in such a way that the differentiation of these stem cells is guided along said third nanoparticles in the third orientation of growth, preferably the same second orientation of growth X2.

Figure 4:
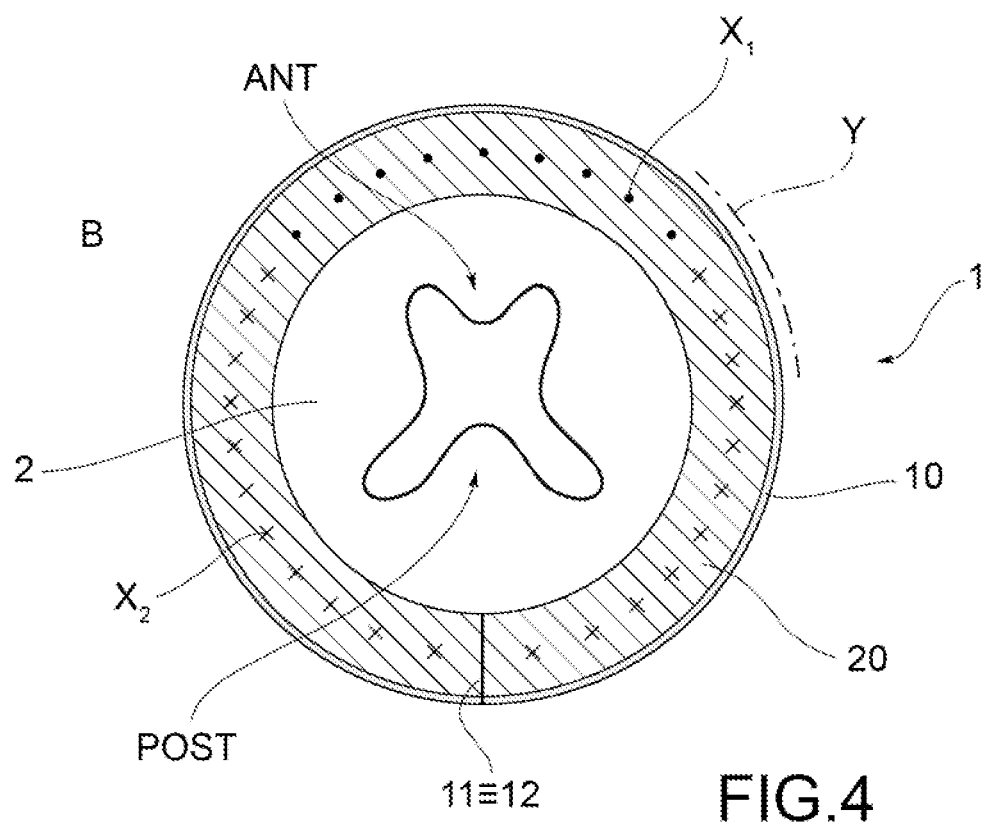
FIG. 4 shows a sectional view along the transverse plane of a medical device in accordance with an embodiment of the present invention wrapped around the spinal cord, wherein a point indicates a craniocaudal orientation, while a cross indicates a caudocranial orientation.
Figure 5:
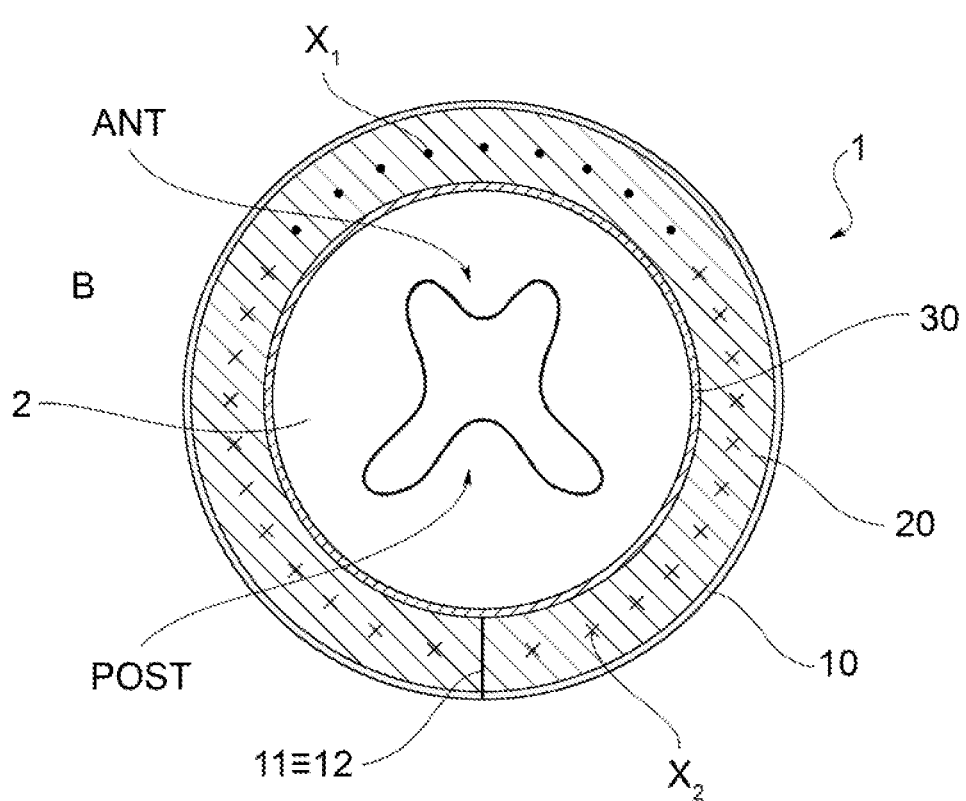
FIG. 5 shows a sectional view along the transverse plane of a medical device in accordance with a second variant embodiment of the present invention wrapped around the spinal cord, wherein a point indicates a craniocaudal orientation, while a cross indicates a caudocranial orientation.

In this variant embodiment, when the medical device is implanted around the spinal cord in a wrapped configuration (i.e. with the two flexible ends 11 and 12 of the substrate joined together, as shown in FIGS. 4 and 5), the region N2 is adjacent to the anterior region ANT of the spinal cord, whereby the differentiation of stem cells is promoted in the first orientation of growth X1, i.e. in the craniocaudal (or efferent) orientation, while the regions N1 and N3 are adjacent to the posterior region POST of the spinal cord, whereby the differentiation of the stem cells is promoted in the second orientation of growth X2, i.e. in the caudocranial (or afferent) orientation.

In a preferred variant embodiment, the first and/or second and/or third nanoparticles comprise or are entirely carbon nanotubes.

Preferably the first flexible substrate 10 is a strip of dura mater, or of swine or bovine or equine pericardium, or of fasciae latae of the leg.

Preferably, the stem cells comprise autologous stem cells of a patient in whom the medical device 1 is implanted, obtained from the patient's adipose tissue or from the patient's cartilage, bone marrow or epidermis.

In a preferred variant embodiment, the first and/or second and/or the third nanoparticles are totally embedded in the binding layer 20, whereby when the medical device 1 is in its configuration wrapped around the spinal cord 2 or peripheral nerve, such nanoparticles are not in direct contact with the spinal cord 2 or the peripheral nerve. This tactic reduces the risk of toxicity of the nanoparticles on the spinal cord or nerve.

In a further variant embodiment, for example shown in FIG. 5, the medical device also comprises a second flexible substrate 30, for example made of the same material as the first flexible substrate 10. This second flexible substrate 30 is arranged facing the first flexible substrate 10 and is also joined to the binding layer 20 whereby the binding layer 20 is interposed between the first flexible substrate 10 and the second flexible substrate 30.

The second flexible substrate 30 is intended to come directly in contact with the spinal cord 2 or the peripheral nerve. The presence of the second flexible substrate 30 further reduces the risk of toxicity of the nanoparticles on the spinal cord, by interposing an additional barrier layer.

In accordance with one embodiment, the first flexible substrate 10 and/or the second flexible substrate 30 is a thin substrate that extends over a plane predominantly along a predominant direction of extension Y and which comprises a lower margin 13 and an upper margin 14 that extend predominantly along the predominant direction of extension Y. The lower margin 13 and the upper margin 14 are spaced along the minor direction of extension X", perpendicular to the predominant direction of extension Y. For example, the flexible substrate 10 and/or the second flexible substrate 30 is an elongated or rectangular or ellipsoidal or rectangular substrate with rounded corners. In this variant, therefore, the first orientation of growth X1 is substantially statistically perpendicular to the predominant direction of extension Y and has an orientation of growth that proceeds from the upper margin 14 to the lower margin 13. In the variant that comprises second silicon nanoparticles, the second orientation of growth X2 is also substantially statistically perpendicular to the predominant direction of extension Y but has an orientation of growth opposite to the first orientation of growth X1, i.e. from the lower margin 13 to the upper margin 14.

Thus, preferably in the variant that comprises the third region N3, near to a right end 12 of the first flexible substrate 10, the third nanoparticles are oriented in such a way that the preferential direction of development X of each third nanoparticle is statistically identical to the second orientation of growth X2, i.e. from the lower margin 13 to the upper margin 14.

In one advantageous embodiment, the first flexible substrate 10 and/or the binding layer 20 and/or the second flexible substrate 30 contains a molecule comprising a nitrous group, whereby said molecule releases nitric oxide in direct form or in contact with the water environment of the spinal canal. In this embodiment, nitric oxide generates a vasodilatory action with an increase in vascularization and consequent reduction of secondary inflammatory damage and an improved repairing action of stem cells on the spinal cord.

The preparation of the medical device, in an embodiment thereof, provides therefore for preparing the first flexible substrate 10 on which the oriented and functionalized nanoparticles are adhered, providing a mixture of autologous stem cells and binding material on the first flexible substrate 10, so as to form the binding layer 20 and so as to incorporate the nanoparticles.

Preferably, the preparation further provides for providing a second flexible substrate on the binding layer 20 so as to close "in a sandwich" the binding layer between the first and second flexible substrate.

According to a further aspect, a method of implanting a medical device previously described for the repair of the spinal cord or a peripheral or central nerve is also the subject of the present invention.

In the case of spinal cord surgery, the method comprises the steps of: performing a dorsal laminectomy in the vicinity of a lesion to expose the dural sac; opening the dural sac and exposing the spinal cord; possibly anchoring the dural flaps to the muscle walls; possibly sectioning the denticulated ligaments to allow easier access; inserting the medical device 1 whereby it is wrapped completely around the spinal cord, for example, as a shirt collar around the neck.

Figure 1A:
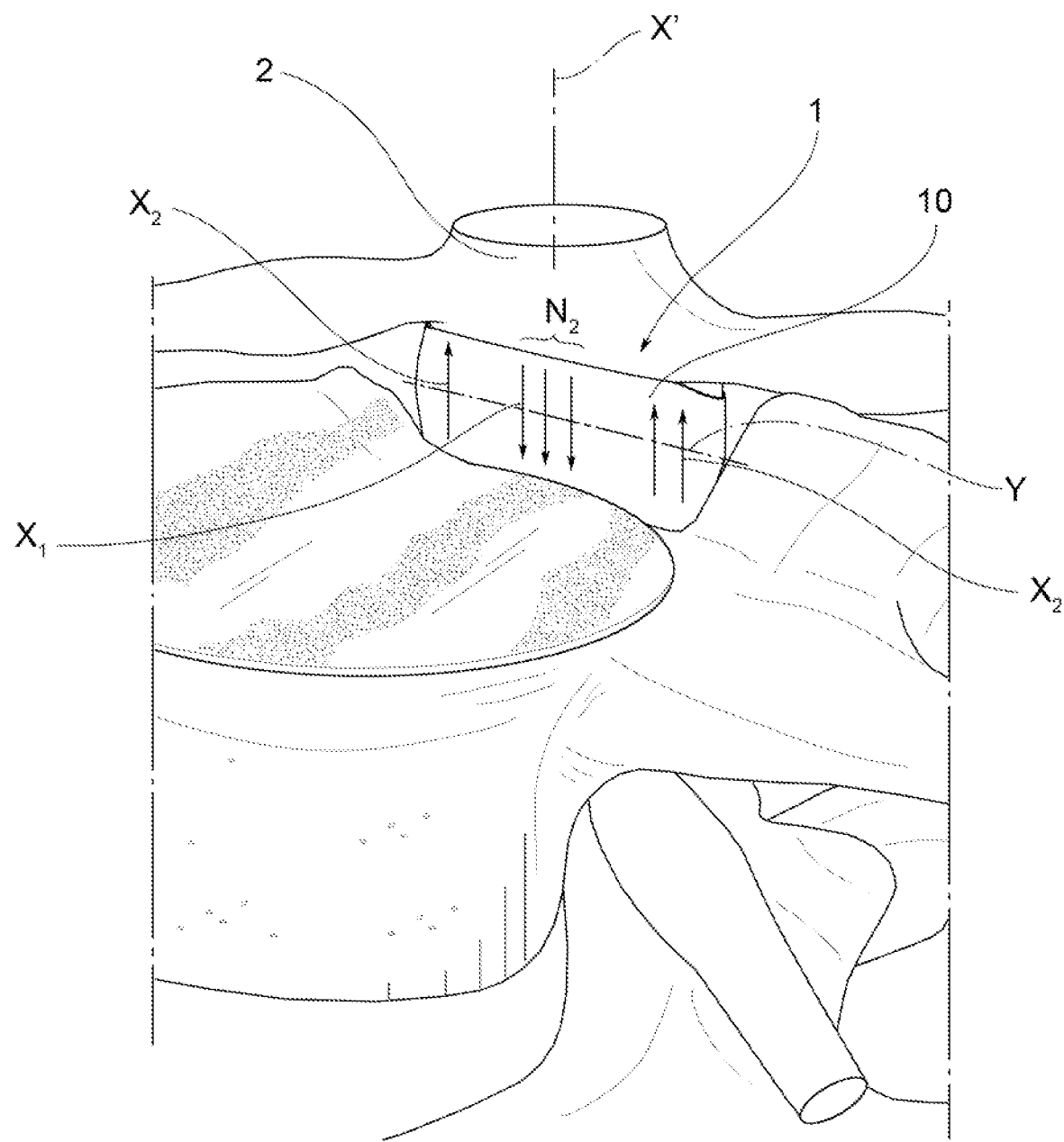
FIG. 1a shows a perspective view of a medical device in accordance with an embodiment of the present invention, implanted and wrapped around the spinal cord.

Preferably, the medical device is inserted by sliding one end 11 or 12 of the flexible substrate 10 from one side of the spinal cord towards the anterior region ANT until it emerges from the opposite side of the spinal cord (as shown, for example, in FIG. 1). Once this operation has been performed, the two ends 11 and 12 of the flexible substrate are joined, for example, by suturing in the vicinity of the posterior region POST of the spinal cord, whereby the device is completely wrapped around the spinal cord (as shown, for example, in FIGS. 1a, 4 and 5).

One thus proceeds to the known stages of reclosing the dural sac and the remaining tissues of the access opening.

Innovatively, the present invention allows neuronal regeneration in the vicinity of a nerve or spinal cord lesion to be improved and promoted.

In particular, the medical device according to the present invention provides a substrate for the growth of stem cells, guiding the correct direction of growth. Moreover, as the nanoparticles are bound to the flexible substrate, there is no risk that these nanoparticles will migrate toward other regions, thus reducing the risk of any toxicity.

Furthermore, the possibility of functionalizing differently in specific regions of the medical device allows the differentiation and growth of the stem cells to be guided in a specific way for each region of the spinal cord (motor or sensory) on a single medical device. Therefore, with a single device and with a single operation, it is possible to intervene also on lesions that affect both the efferent and afferent neuronal fibers.

Moreover, in the case of restoration of a lesion of a peripheral or generic central nerve, wherein it is not possible to establish preferred regions of orientation of the neuronal fibers, the presence of regions with alternating orientation of the nanoparticles on a single medical device allows the growth of cells to be promoted both in one direction and in the opposite direction, so as to increase the possibility that at least one group of neurons will be oriented in one of the two directions, promoting the reconnection.

Furthermore, the presence of fibrin, or Lyodura, or polyamides, or polylacticates, or an equivalent material allows direct contact between the nanotubes and the spinal cord or nerve to be avoided, thus avoiding any possible toxicity from the carbon or the silicon or gold metals of the nanotubes.

It is clear that a person skilled in the art, in order to satisfy contingent and specific needs, may make changes to the invention described above, all of which are, however, contained within the scope of protection as defined by the following claims.

The invention claimed is:

1. A method for implanting a medical device for repairing an injury to the spinal cord, the medical device comprising a first biological or biocompatible flexible substrate which supports first nanoparticles selected from the group consisting of silicon, carbon, gold, and titanium, at least partially embedded in a binding layer made of binding material, said binding layer being joined to the first biological or biocompatible flexible substrate, wherein each first nanoparticle of said first nanoparticles extends along a preferential direction of development (X) and wherein the first nanoparticles are oriented so that, statistically, said preferential direction of development (X) of each first nanoparticle is parallel to a first orientation of growth (X1), and wherein stem cells are at least partially embedded in said binding layer and said first nanoparticles are functionalized so that differentiation of said stem cells is guided along said first nanoparticles in the first orientation of growth (X1); wherein the first biological or biocompatible flexible substrate is suitable to assume a distended configuration and a wrapped configuration, and wherein, in said wrapped configuration, the first biological or biocompatible flexible substrate is wrapped around the spinal cord whereby said first orientation of growth (X1) is statistically parallel to a neuronal direction (X') of extension of neurons of the spinal cord, said method comprising:

performing a dorsal laminectomy in the vicinity of a lesion to expose the dural sac;

opening the dural sac and exposing the spinal cord; and inserting the medical device by sliding one end of the first biological or biocompatible flexible substrate from one side of the spinal cord towards an anterior region until it emerges from an opposite side of the spinal cord, whereby the medical device is wrapped around the spinal cord.

2. The method of claim 1, wherein, once the medical device has been inserted, both ends of the first biological or biocompatible flexible substrate are joined whereby the medical device is completely wrapped around the spinal cord.

3. The method of claim 1, wherein further comprising sectioning denticulated ligaments prior to said inserting.

\* \* \* \* \*